United States Patent [19]
Bencini et al.

[11] Patent Number: 5,976,164
[45] Date of Patent: Nov. 2, 1999

[54] METHOD AND APPARATUS FOR MYOCARDIAL REVASCULARIZATION AND/OR BIOPSY OF THE HEART

[75] Inventors: Robert F. Bencini, Sunnyvale; Richard L. Mueller, Byron; Richard D. Phipps, Morgan Hill, all of Calif.

[73] Assignee: Eclipse Surgical Technologies, Inc., Sunnyvale, Calif.

[21] Appl. No.: 08/908,816

[22] Filed: Aug. 8, 1997

Related U.S. Application Data

[63] Continuation-in-part of application No. 08/713,531, Sep. 13, 1996.

[51] Int. Cl.$^6$ ........................................... A61B 17/00
[52] U.S. Cl. ........................... 606/170; 606/159; 606/180
[58] Field of Search ................... 606/1, 108, 167, 606/170, 171, 180; 600/564–568

[56] References Cited

U.S. PATENT DOCUMENTS

| | | |
|---|---|---|
| 4,461,305 | 7/1984 | Cibley . |
| 4,576,162 | 3/1986 | McCorkle . |
| 4,658,817 | 4/1987 | Hardy . |
| 4,850,354 | 7/1989 | McGurk-Burleson et al. . |
| 5,263,959 | 11/1993 | Fischell . |
| 5,358,472 | 10/1994 | Vance et al. . |
| 5,366,468 | 11/1994 | Fucci et al. . |
| 5,380,316 | 1/1995 | Aita et al. . |
| 5,403,311 | 4/1995 | Abele et al. . |
| 5,477,862 | 12/1995 | Haaga . |
| 5,591,159 | 1/1997 | Taheri . |
| 5,632,755 | 5/1997 | Nordgren et al. . |
| 5,658,272 | 8/1997 | Hasson . |
| 5,702,412 | 12/1997 | Popov et al. .............................. 606/159 |
| 5,741,287 | 4/1998 | Alden et al. . |
| 5,794,626 | 8/1998 | Kieturakis .............................. 600/567 |
| 5,807,277 | 9/1998 | Swaim . |

FOREIGN PATENT DOCUMENTS

| | | |
|---|---|---|
| 0 807 412 | 11/1997 | European Pat. Off. . |
| WO 96/35469 | 11/1996 | WIPO . |
| WO 98/19614 | 5/1998 | WIPO . |

*Primary Examiner*—Michael Buiz
*Assistant Examiner*—William Lewis
*Attorney, Agent, or Firm*—Janet Kaiser Castaneda

[57] ABSTRACT

A semi-automatic cardiac tissue removal device for obtaining biopsy samples and/or creating revascularization pathways in the myocardium of the heart, mechanically cuts the pathways using a handpiece with a cutting tip assembly having a hollow needle with an angled, sharpened edge rotatable mounted around a separately advancable stylet. The stylet defines a piercer to spread the myocardium prior to insertion of the needle and to allow creation of a pathway only within the myocardium. The stylet further defines a plug at the cutting edge of the needle to finish the cutting cleanly and to plug the hollow needle thereby forming a closed chamber for excised tissue. A single button on the left or right handed handpiece actuates movement of the stylet into the myocardium, movement of the needle into the path produced by the piercer, and rotation of the needle to cut tissue.

32 Claims, 18 Drawing Sheets

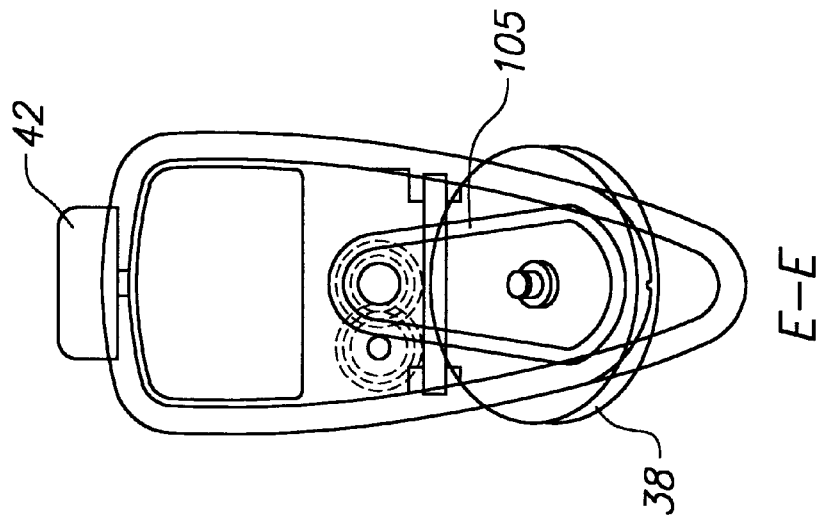
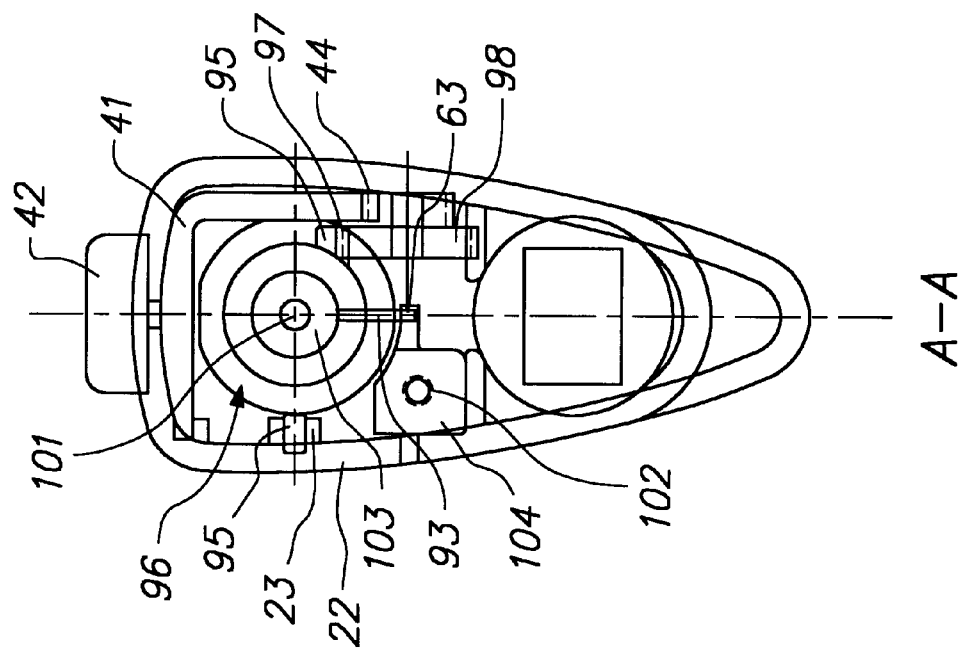
FIG. 2F
FIG. 2D

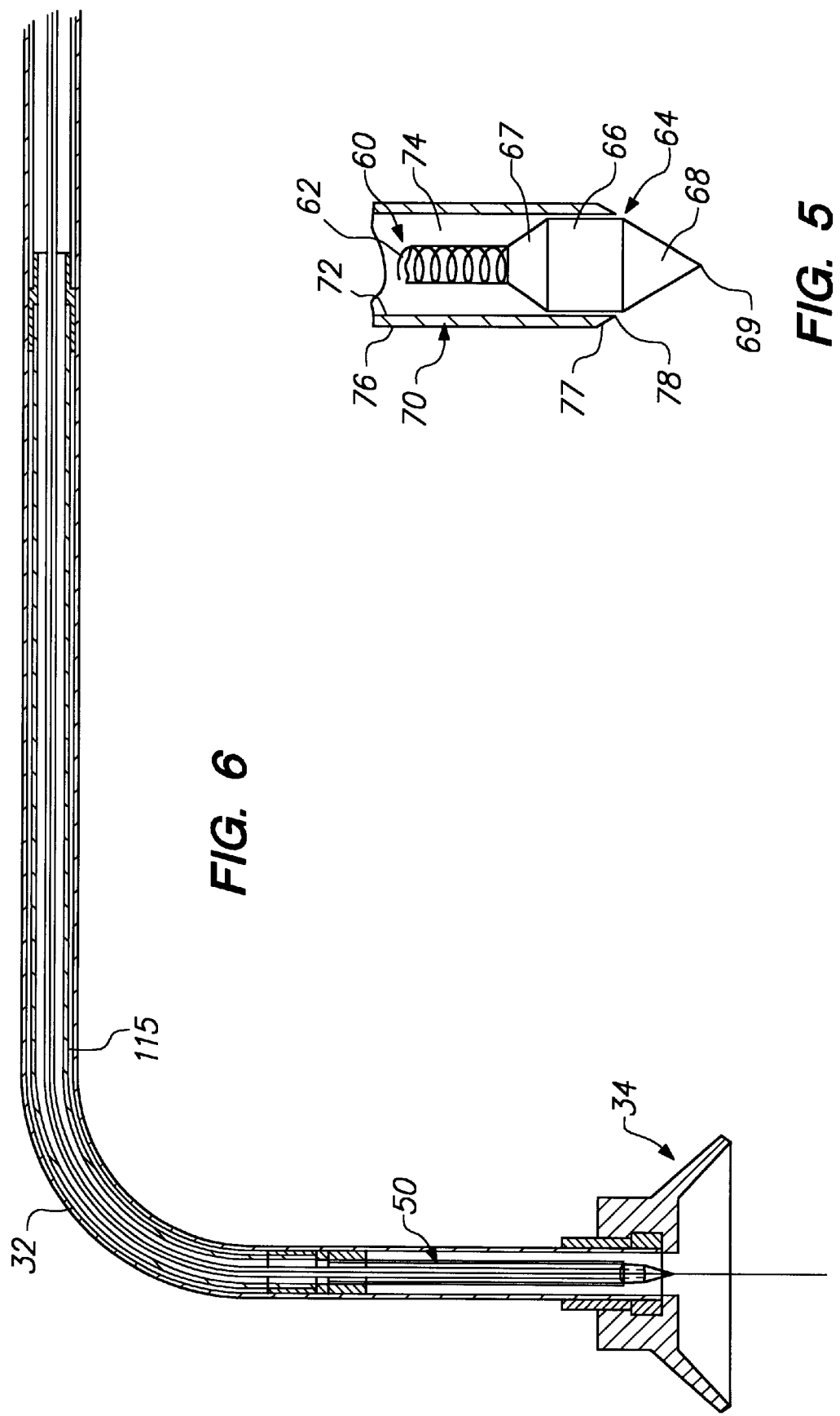

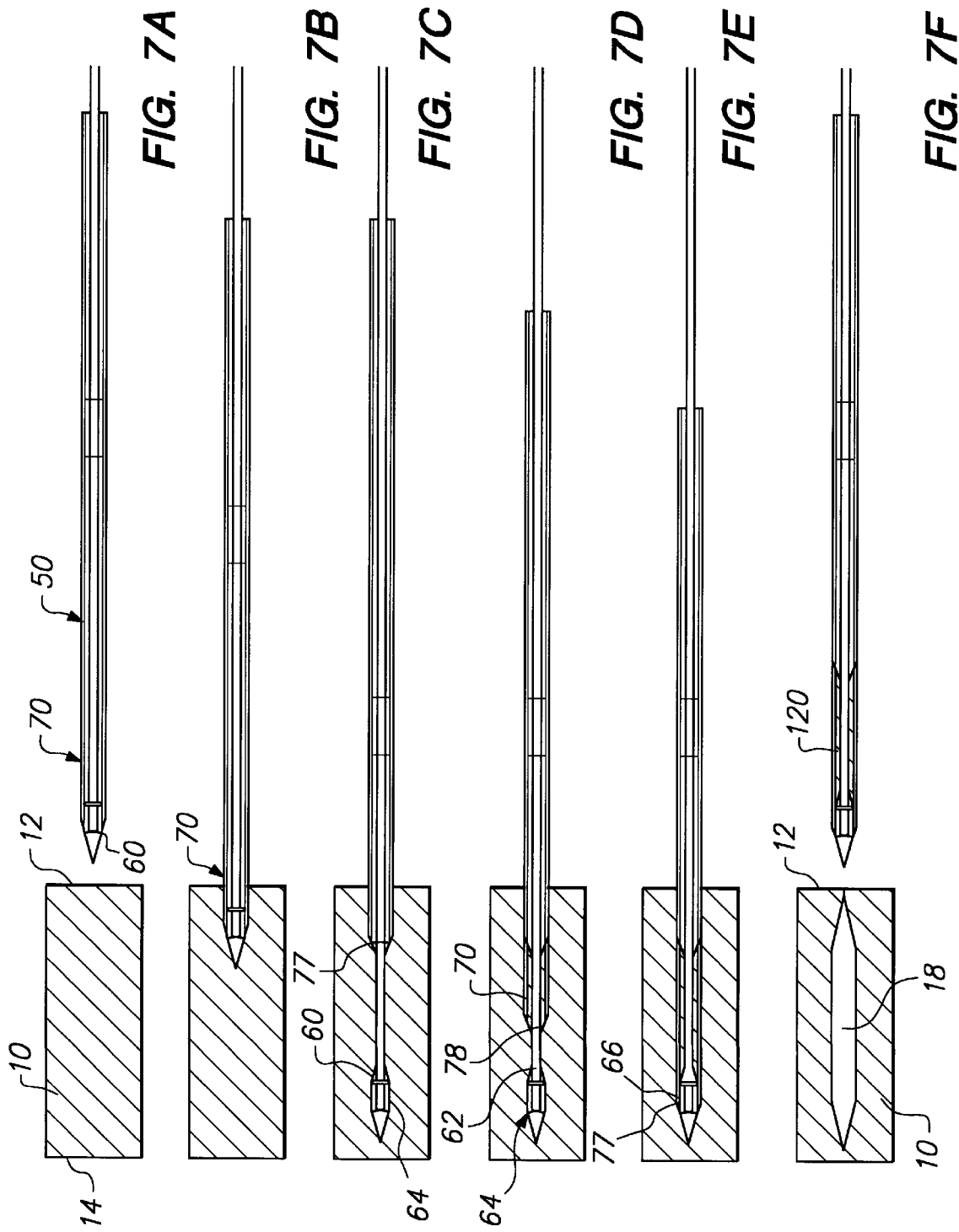

METHOD AND APPARATUS FOR MYOCARDIAL REVASCULARIZATION AND/OR BIOPSY OF THE HEART

RELATED APPLICATIONS

This application is a continuation-in-part of U.S. patent application Ser. No. 08/713,531, filed on Sep. 13, 1996, allowed.

FIELD OF THE INVENTION

This invention relates to the field of mechanical tools for cardiac surgery, and more particularly to non-laser methods and devices for myocardial revascularization and/or tissue biopsy of the heart.

BACKGROUND OF THE INVENTION

Heart disease is a significant health problem which has been the subject of substantial medical study. Bypass surgery has become commonplace; yet such surgery may be unavailable to many patients, either because of the nature of the occlusions or the physical condition of the patient.

One promising alternative technique for treating such cases is known as transmyocardial revascularization (TMR). Although this technique was considered as early as the work of Dr. C. Beck "the Development of a New Blood Supply to the Heart By Operation", *Annals of Surgery*, Vol. 102, No. 5 (11/35) pp. 801–813, the method was not extensively studied until the work of Dr. M. Mirhoseini and M. Cayton, an example of which is found in "Lasers in Cardiothoracic Surgery in *Lasers in General Surgery* (Williams and Williams; 1989) pp. 216–223.

Clinical tests have demonstrated that TMR channels, which generally communicate with the ventricle, facilitate revascularization of the heart muscle and recovery of heart function. Recent studies further demonstrate that beneficial revascularization also occurs following creation of channels that do not remain patent and channels that do not communicate with the ventricular chamber.

A laser device to perform TMR is described in Aita et al., U.S. Pat. No. 5,380,316, issued Jan. 10, 1995. In the procedure described in that patent, a number of channels are formed through the epicardium by means of a laser apparatus to extend through the myocardium to communicate with the ventricle. Other laser patents describing surgical transmyocardial revascularization include U.S. Pat. Nos. 5,554,152 and 4,658,817.

Unfortunately, laser techniques have some attendant difficulties. The laser equipment for performing such procedures is generally expensive, and, in some cases the lasers are large and cumbersome. Such lasers may be unavailable to smaller and more remote medical facilities. Some patients may therefore find it difficult to gain access to a properly equipped medical facility when treatment is needed. Additionally, lasing through the epicardium or endocardium, as described in many laser TMR procedures, may result in some destruction of viable vascular tissue contiguous to the epicardium or endocardium.

One alternative to the use of lasers would be to use a mechanical cutter to produce the channels. Early prior art methods of mechanical piercing and cutting of the heart wall were not pursued further because mechanical cutting did not produce patent channels.

A recent laser TMR device to perform transmyocardial revascularization includes some non-laser mechanisms and is described in PCT Patent Application Publication No. WO 96/35469. The PCT application briefly shows a mechanical auger, mechanical abrasion device, heat, a fluid jet, and a rotary toothed blade for mechanical TMR using a percutaneous approach. The mechanical devices described may produce an irregular cut in the myocardium which may result in leaving tissue flaps or fragments in the channel or ventricle. Such debris possibly could lead to life threatening emboli.

Commonly owned, co-pending U.S. patent application Ser. No. 08/713,531, filed on Sep. 13, 1996, describes mechanical TMR using cutting devices comprised of inner hollow needles or drill tipped devices mounted within outer hollow needles for transmyocardial revascularization. Additionally, a single rotating, hollow needle is described. A sharp cutting blade is used to produce a clean cut, although no specific mechanism is provided to positively ensure that tissue flaps do not remain. Commonly owned, copending U.S. patent application Ser. No. 08/773,778, filed on Dec. 26, 1996, also describes a mechanical cutting device used in conjunction with a laser to create drug delivery pockets and/or stimulation zones within myocardium. The laser is used to introduce the cutting device into the myocardium, and the cutting device defines two, hollow halves that snap together to cut tissue, which is trapped between the halves, to form pockets.

It would be desirable to produce clear, clean revascularization pathways that may be formed only in myocardium, if desired, while ensuring that excised tissue is cleanly removed without leaving tissue flaps and debris behind, using a relatively inexpensive and easily transportable mechanical heart surgical device suitable for heart biopsy and non-laser myocardial revascularization.

SUMMARY OF THE INVENTION WITH ADVANTAGES

Broadly, an advantage of the present invention is to provide an apparatus and method for mechanically excising myocardial tissue from the heart to produce myocardial revascularization pathways and biopsy samples.

More specifically, an advantage of the present invention is to provide an apparatus and method for mechanically performing myocardial revascularization by cleanly cutting pathways to prevent debris and/or remaining tissue flaps which may cause emboli or other complications.

It is a further advantage of the present invention to provide an apparatus and method for mechanically performing myocardial revascularization without a requirement for large, expensive laser equipment.

Yet another advantage of the present invention is to provide a mechanical cardiac tissue removal device having a stylet with a tissue piercing and spreading tip which minimizes trauma by creating an opening into myocardium for a rotating hypotube surrounding the stylet, the stylet and needle cooperating to cleanly cut and secure excised tissue, the hypotube configured to require reduced tissue insertion force.

Still one more advantage of the present invention is to provide a powered mechanical cardiac tissue removal device configured for single handed use to create pathways in myocardium without substantial damage to or removal of tissue from the outer layers of the heart or from the tissue surrounding the created pathway.

Yet one more advantage of the present invention is to provide a mechanical cardiac tissue removal device which retains excised myocardial tissue for subsequent biopsy analysis.

An additional advantage of the present invention is to provide a mechanical cardiac tissue removal device which enables creation of revascularization pathways solely within the myocardium.

The present invention comprises a method and apparatus for mechanically performing cardiac tissue biopsy and/or mechanical myocardial revascularization. Myocardial revascularization is herein defined to include creating revascularization channels within or extending entirely through the myocardium as well as creating stimulation zones in the myocardium which result in revascularization but are not expected to remain completely patent for extended periods. Revascularization channels and/or stimulation zones are herein referred to as "pathways". It will be understood that the creation of such pathways results in collection of tissue samples suitable for biopsy.

Although the invention may be implemented in a variety of embodiments, several of which are illustrated herein, all require a mechanical device with a special cutting tip assembly comprising a stylet surrounded by a hypotube which is defined as a hollow tube such as hypodermic tubing. The stylet has a piercer which pierces and/or spreads the layer of tissue covering the myocardium of the heart and creates an entry path for the hypotube when the stylet is advanced into the myocardium. The hypotube defines a cutting edge which cleanly cuts a core of myocardial tissue as the hypotube preferably is rotated into the myocardium. The geometries of the cutting edge and stylet together allow the edge and stylet to cooperatively and cleanly excise myocardial tissue without leaving tissue flaps or fragments. Additionally, the geometries create a chamber surrounding the excised tissue thereby producing a clean pathway following removal of the cutting tip assembly and excised tissue. The excised tissue is held by the stylet which is configured to allow creation of multiple pathways prior to removal of stored, excised tissue.

The operating mechanism for the cutting tip assembly is housed in a hand piece which has an atraumatic tissue contact portion for supporting the cutting tip assembly in location on the heart wall while in operation. In at least one of the embodiments shown herein, the contact portion may include one or more suction conduits to assist in clean, complete, removal of the material excised from the heart wall by the cutting tip assembly during formation of pathways. Additionally, means for delivering therapeutic substances, such as cardiovascular agents or flushing solutions, to the created pathways may be provided.

Preferably, the cutting tip assembly is removably mounted to the hand piece which defines one or more manual or powered actuators to deploy, rotate, and remove the cutting tip assembly.

The cutting tip assembly optionally may be heated to provide thermal damage to the heart muscle during the creation of the pathway.

In its simplest aspect which is particularly suitable for biopsy purposes, suction is not used, therapeutic conduits are not provided, and the cutting tip assembly is not heated. Additionally, the cutting tip assembly need not be removable in this aspect and the depth stop mechanism may be simplified to provide a maximum depth only.

These and other objects, advantages and features of the present invention will be apparent to those skilled in the art from the following detailed description and the accompanying drawings.

BRIEF DESCRIPTION OF THE DRAWINGS

FIGS. 2C and 2D are, respectively, a side view of the components of the handpiece of the device, showing the spring component of the sequencing bar, and a cross sectional view taken along lines A—A of FIG. 2C. FIG. 2F is a cross sectional view of the depth control setting mechanism taken along lines E—E of FIG. 2C.

FIG. 5 is an enlarged view of the distal end of a referred cutting tip assembly showing the positions of the cooperating distal end of the stylet and the cutting edge of the hypotube at completion of a cutting operation.

FIG. 6 is a side sectional view of the torquable shaft portion of the mechanical cardiac tissue removal device.

FIGS. 7A–7F are sequential views of the cutting tip assembly entering and exiting tissue to create a pathway or take a tissue sample.

DETAILED DESCRIPTION OF THE PRESENT INVENTION

Figure 1A:
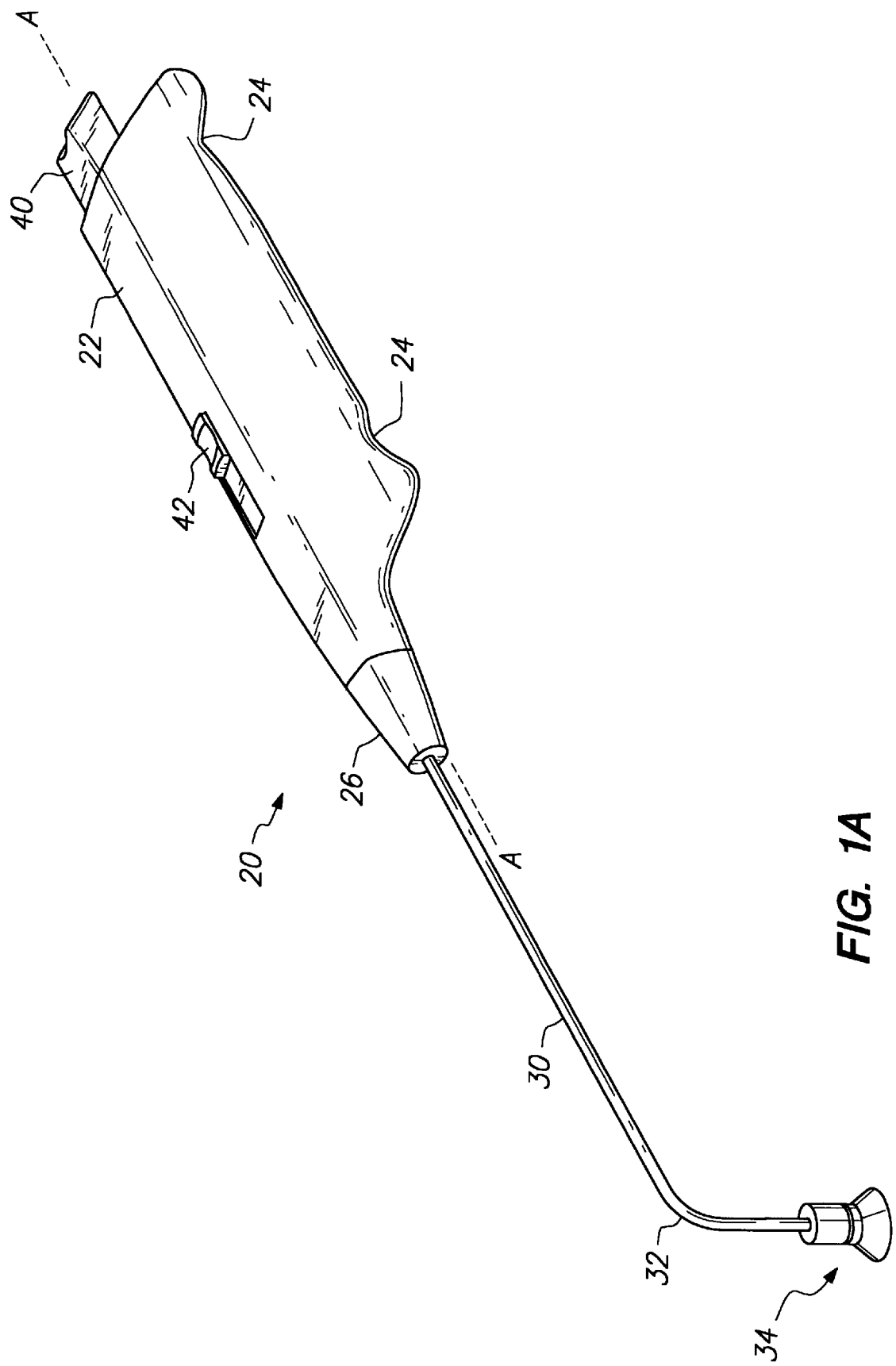
FIGS. 1A, 1B and 1C are, respectively, perspective views of a presently preferred mechanical cardiac tissue removal device showing the atraumatic tissue contact portion and showing alternative single handed grasping positions which may be used to operate the device.
Figure 1B:
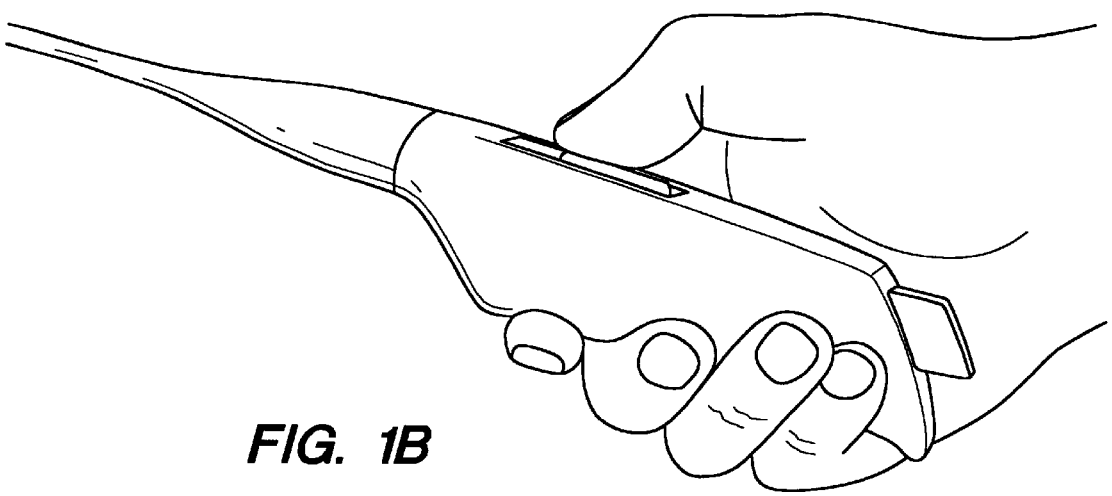
Figure 1C:
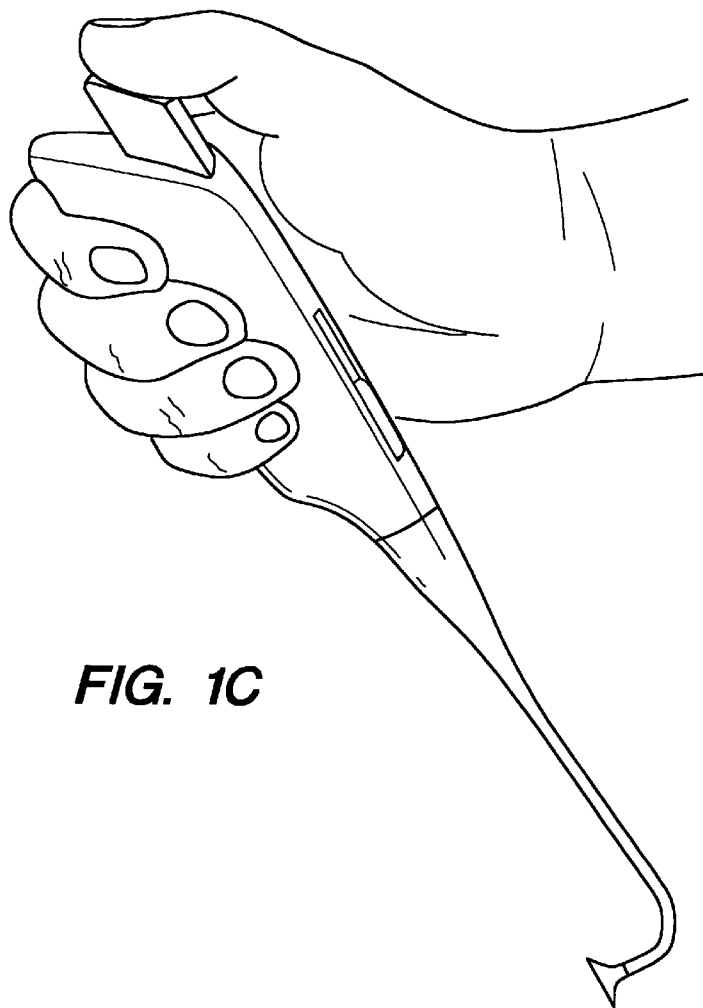

While a variety of embodiments of the present invention are disclosed herein, one exemplary presently preferred embodiment of a mechanical cardiac tissue removal device suitable for biopsy and/or myocardial revascularization is illustrated generally as reference number 20 in FIGS. 1A–1D. The cardiac tissue removal device 20 is particularly suitable for surgical or minimally invasive(MIS) myocardial revascularization and/or biopsy and may be held in the hand in several positions, as illustrated in FIGS. 1B and 1C, for single handed, left or right hand, operation to obtain biopsy samples or create myocardial revascularization pathways. As defined herein, a pathway means a revascularization channel which extends into myocardium, may or may not communicate with the ventricle, and a stimulation zone or channel which results in revascularization but is not expected to remain completely patent for extended periods. The semi-automatic device 20 perforates the epicardium of the heart, places the stylet within the myocardium, rotates and advances the hypotube around and over the stylet, and captures the excised tissue within the device for complete removal, as described in detail below.

Figure 8A:
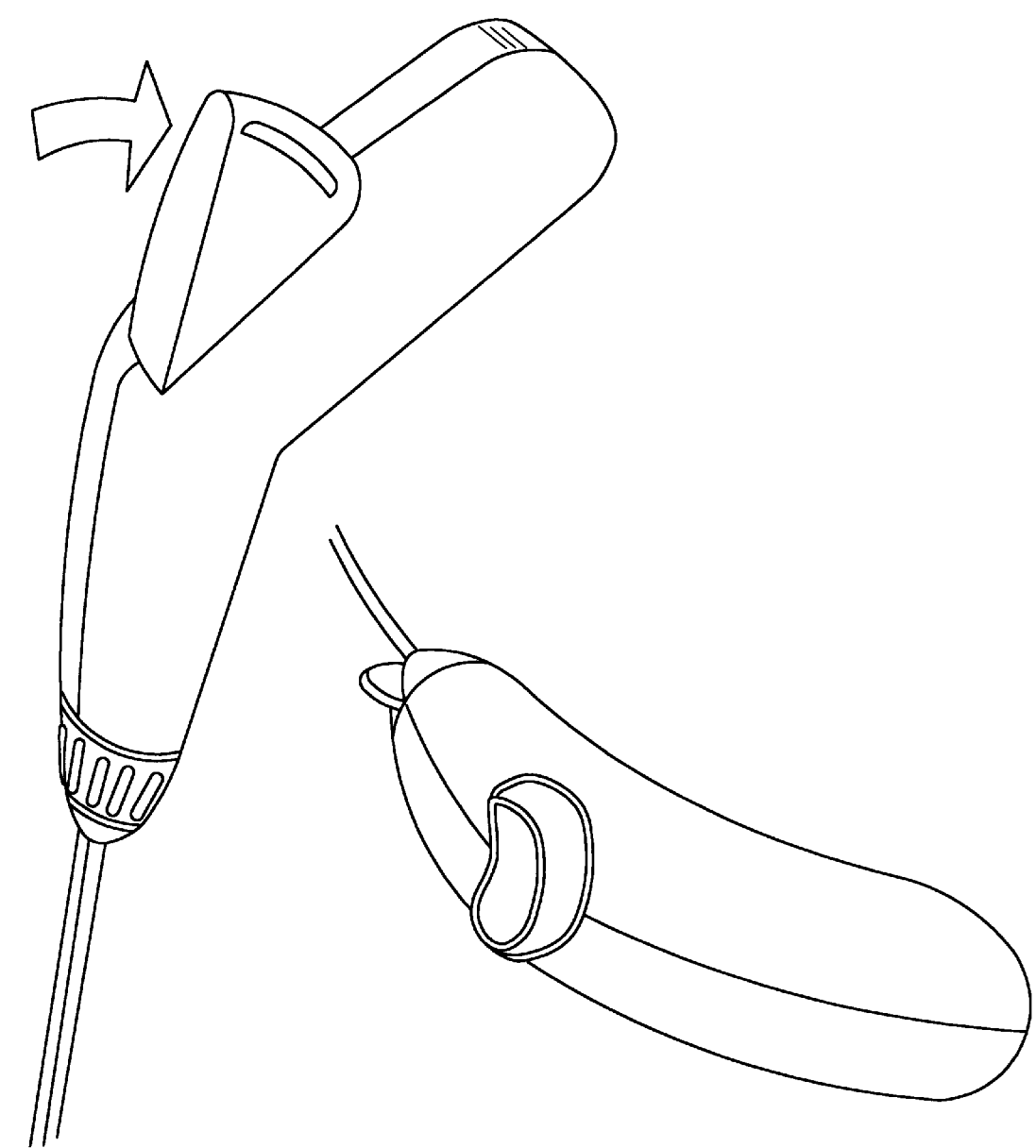
FIGS. 8A–8E are views of alternative housings for a mechanical cardiac tissue removal device.
Figure 8B:
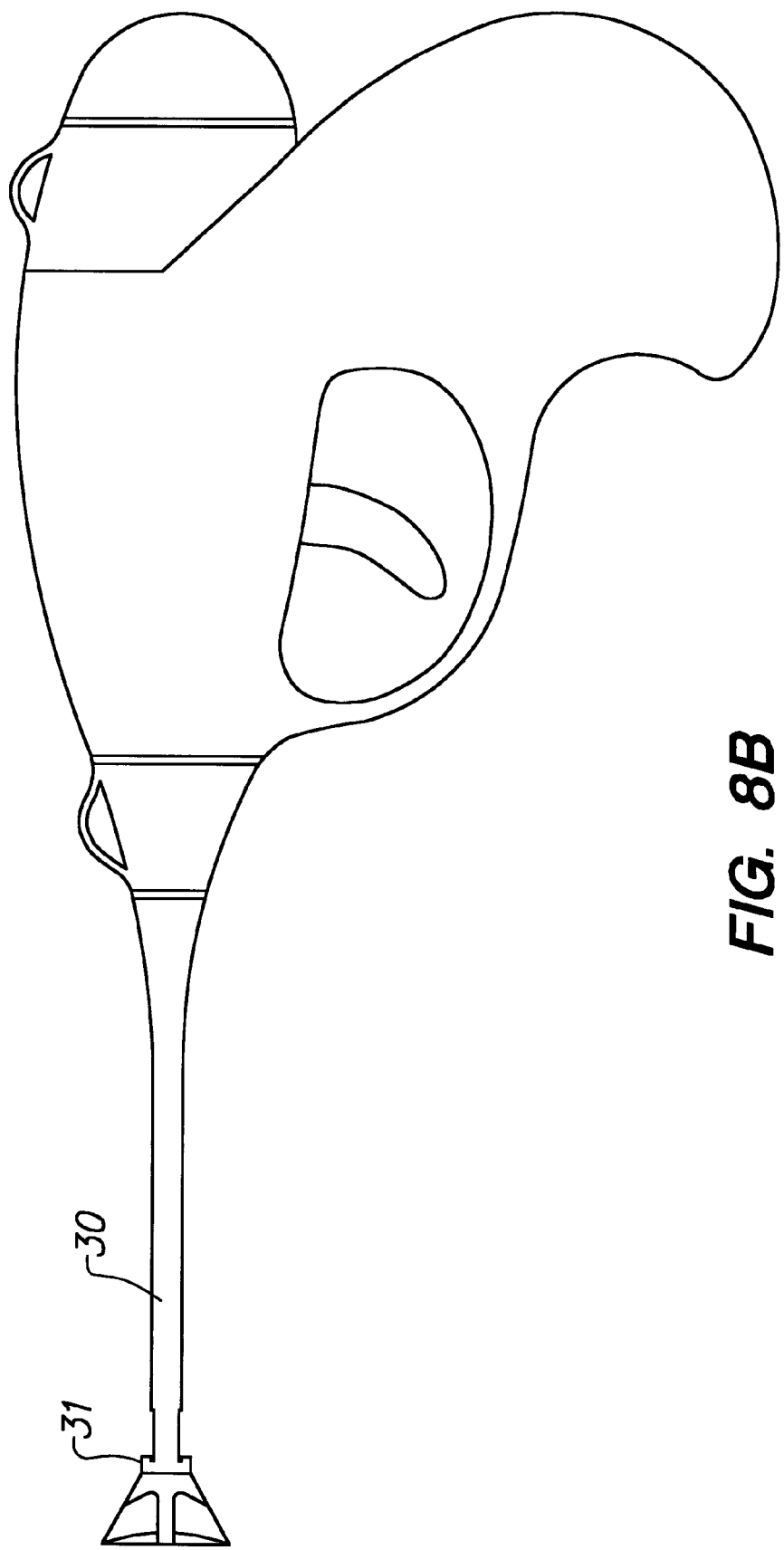
Figure 8C:
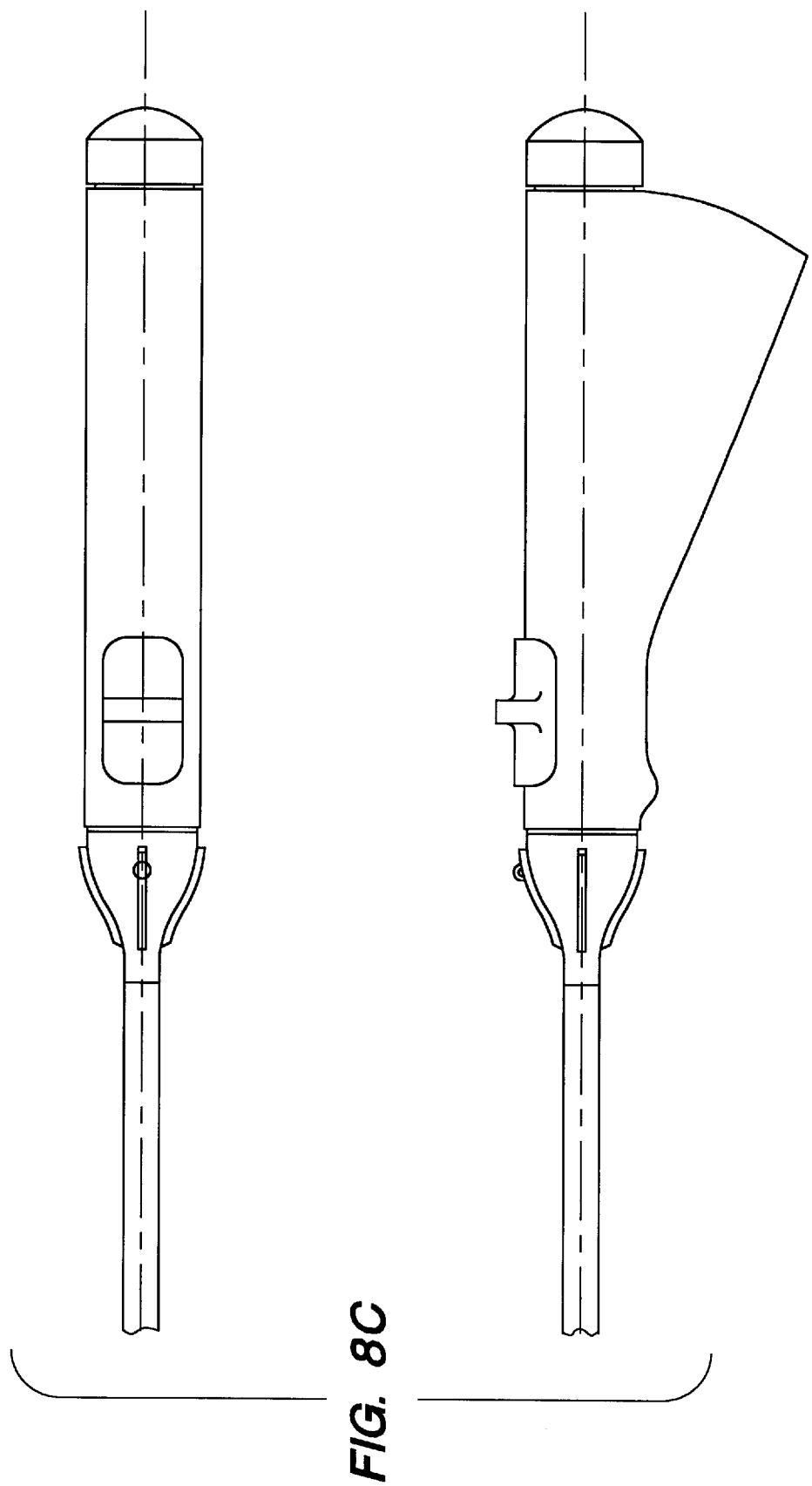
Figure 8D:
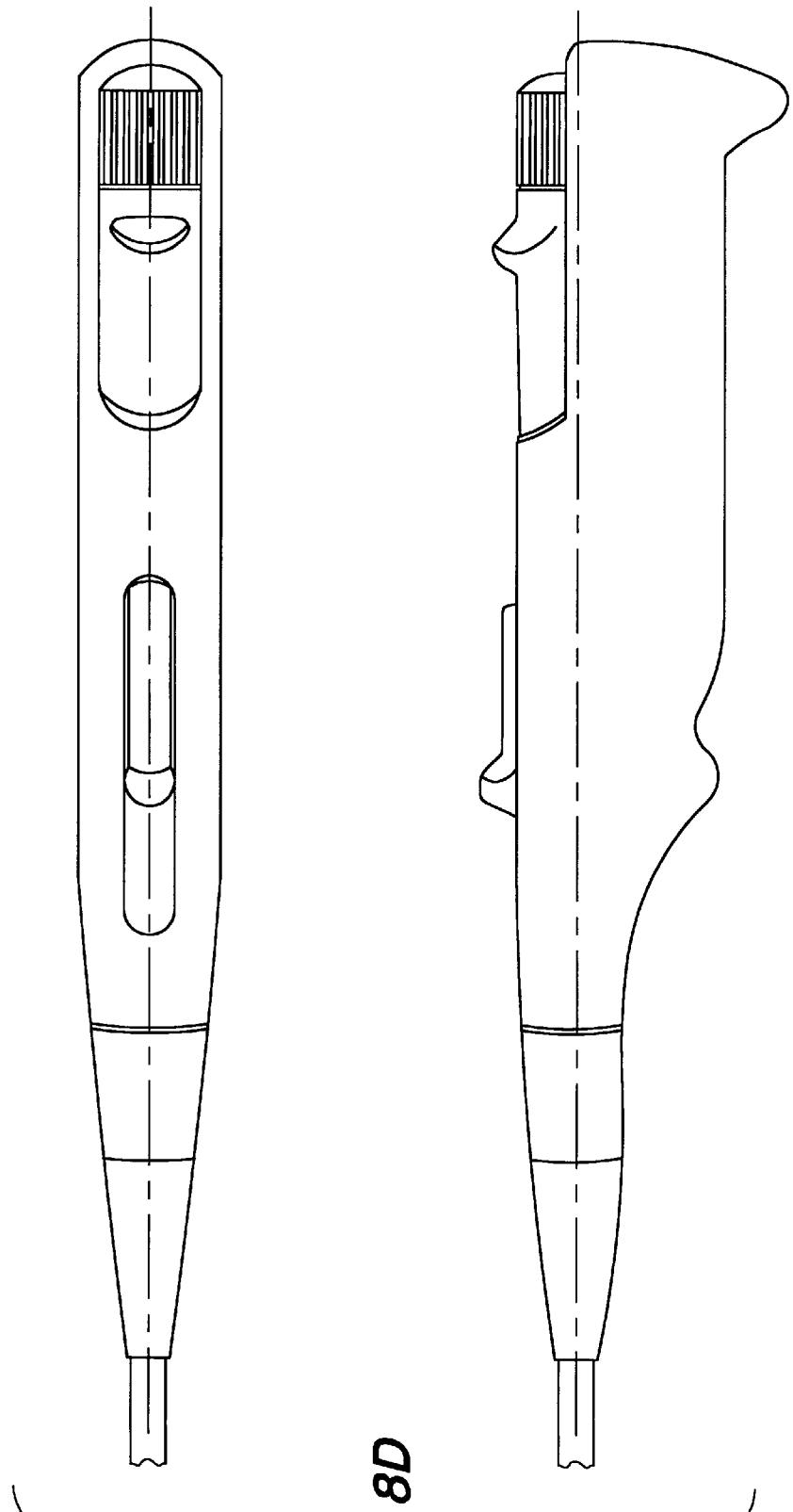
Figure 8E:
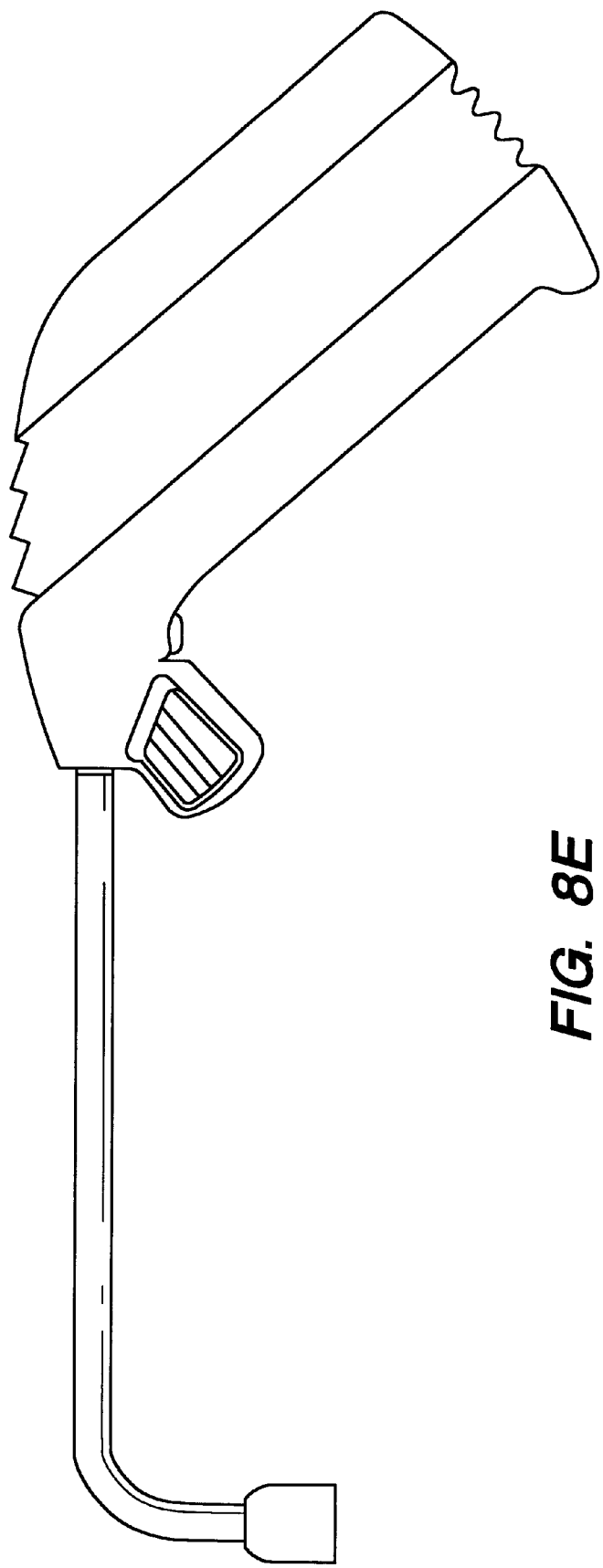

Referring now to FIGS. 1A–1D, the preferred mechanical cardiac tissue removal device 20 includes a hand piece 22 which is a housing molded or machined from a plastic material, and defining a contoured surface defining one or more finger grip indentations 24 which provide tactile feedback regarding the position of the hand on the device so the physician need not look away from the medical procedure. The contoured surface with indentations 24 further assists the user to securely hold the hand piece without slippage in at least two, different positions during either left or right handed operation of the device 20. A tapered neck portion 26 extends from the hand piece 22 and may be a unitary portion of the hand piece 22, or may be separately molded, as shown, and attached to the hand piece 22. A shaft 30 extends outwardly from the neck portion 26. The shaft 30 may be constructed of metal, plastic or composite materials and may be malleable to allow some ability to change the angle of orientation from axis "A". As shown, the torquable shaft 30 defines a generally J-shaped bend 32 and terminates in a protective tip 34. When the neck portion 26 is separately constructed, it may be made rotatable in which case the orientation of the bend 32 and the tip 34 may be altered. Suitable rotation mechanisms include conventional spring fingers, detentsi and ratchet assemblies, such as the ratchet mechanism 28 shown in FIG. 2A, allowing 360° rotation of the tapered nose 26. As an alternative to a curved shaft, the shaft 30 also may be straight if desired as shown in FIG. 8B. A conventional articulating joint 31 may also be included for changing the angle of orientation of the tip portion, particularly when inserting and using the device through a port in a minimally invasive procedure.

The protective tip 34 preferably is generally ball, cup or disc shaped and is designed to contact the heart and maintain contact of the device 20 on the heart during formation of a pathway and/or the taking of a biopsy sample. The protective tip 34 may be constructed from generally yieldable materials such as silicone, soft elastic, rubber or foam and may also be metallic or plastic. The protective tip 34 distributes contact forces on the heart, particularly during beating heart myocardial revascularization, and may be permanently attached to the shaft 30 or may be detachable with conventional snap-mount or screw mount mechanisms. Different detachable tips 34, such as suction and drug delivery tips, may be provided to accommodate size and access interests. The tissue contact surface of the protective tip 34 may be textured to provide a gripping surface, and suction may be provided at the proximal end of the hand piece to extend through the shaft 30 to further secure the protective tip 34 to the heart.

One or more operator buttons or other conventional finger actuated mechanisms extend through the hand piece 22 to operate the cardiac tissue removal device 20. A push button 40 extends out of the proximal end of the hand piece 22 to operate the device in a semi-automatic manner as described below. A second sliding button 42 is operatively connected to the push button 40 thereby allowing operation of the device to be controlled from either of the hand positions shown in FIGS. 1B and 1C. In addition to buttons 40, 42, a depth gauge 36 preferably is provided on the side of the hand piece, and the selection of desired pathway or biopsy depth is controlled by thumb wheel 38 extending through handpiece slot 33. (FIG. 1D) The depth gauge 36 is a sliding knob which protrudes through a slot 31 in the handpiece. Depth markings are provided and may be matched with the position of the slidable knob. Selection of optimum depth for pathways depends upon a number of factors, including but not limited to the depth of the myocardium, the desired depth of the pathway, and whether the pathway is intended to communicate with the ventricle. Generally, the depth stop selector should allow selection of depths between about 0.5 mm to 3.5mm, and selection of a maximum depth of about 2.0 mm to 2.5 mm would avoid communication of a surgically created pathway with the ventricle of the heart. Determination of the depth of the heart wall may be done conventionally prior to performing the myocardial revascularization procedure, or the depth may be determined dynamically during the myocardial revascularization procedure using ultrasound as described in co-pending patent application Ser. No. 08/852,977, filed on May 6, 1997, entitled Ultrasound Device for Axial Ranging, incorporated by reference herein.

Referring now to FIGS. 5 and 7A–7F, following selection of a depth for a desired pathway, a cutting tip assembly 50 (FIG. 3) may be slidably extended through the shaft 30 and out of the protective tip 34 by pressing push button 40 or 42.

The preferred components of the cutting tip assembly 50 comprise a stylet 60 mounted within a hollow hypotube 70. The stylet 60 and the hypotube 70 are preferably sequentially advanced into the heart tissue to create a pathway. The hollow hypotube 70 may be a tapered tube as shown or a conventional biopsy needle, such as a soft tissue biopsy needle. The hypotube 70 defines an interior wall 72 surrounding a lumen 74 and an exterior wall 76. The inner diameter of the lumen may be approximately 0.5 to 2.5 mm depending upon the intended diameter of the pathway. The distal end of the hypotube 70 defines an external beveled portion 77 which terminates to form a sharp cutting edge 78. Rotation of the hypotube 70, as described below, results in a sharp, clean cut by the beveled portion 77 and edge 78. The beveled portion 77 and the edge 78 allow the rotating hypotube 70 to cut through tissue with minimal axial force.

The stylet 60 is mounted for translation within, and extension out of, the lumen 74 and comprises a rod 62 defining a distal plug 64. The stylet preferably is made of metal. The plug 64 defines a generally central body 66 sized to closely fit within the lumen 74 while still allowing easy reciprocation within the lumen. The body 66 further defines a proximal tapered portion 67 extending between the body and the rod 62. The tapered portion 67 self aligns the stylet 60 within the lumen 74. A distal tapered portion 68 extends from the distal end of the body 66 to form a piercer 69. When the hypotube 70 is fully extended around the body 66, as best shown in FIGS. 5 and 7E, the plug substantially closes off the lumen 74 thereby forming a tissue reservoir with support for the excised tissue within provided by the generally central rod 62. As will be seen in conjunction with discussion of operation of the cardiac tissue removal device 20 below, the plug serves several functions. The piercer 69 pierces the heart wall to allow insertion of the hypotube, the rod 62 holds tissue stationary as the tissue collapses in around the rod during cutting, and the body 66, in conjunction with the hypotube 70, finishes off the cutting of a pathway and closes off the distal end of the lumen 74 to form a reservoir for cut tissue.

Referring now to FIG. 6, the cutting tip assembly is advanced through the shaped portion 32 of the shaft 30 using a torquable, bendable shaft insert 115. The torquable insert 115 is a coiled wire spring 182, or wire mesh proximal tubing portion, attached located near the distal end of the cutting tip assembly to provide flexibility to allow the cutting tip assembly to follow the bend 32 in the shaft 30. The torquable shaft insert 115 also may be constructed from a shape memory material such as nitinol.

Figure 2A:
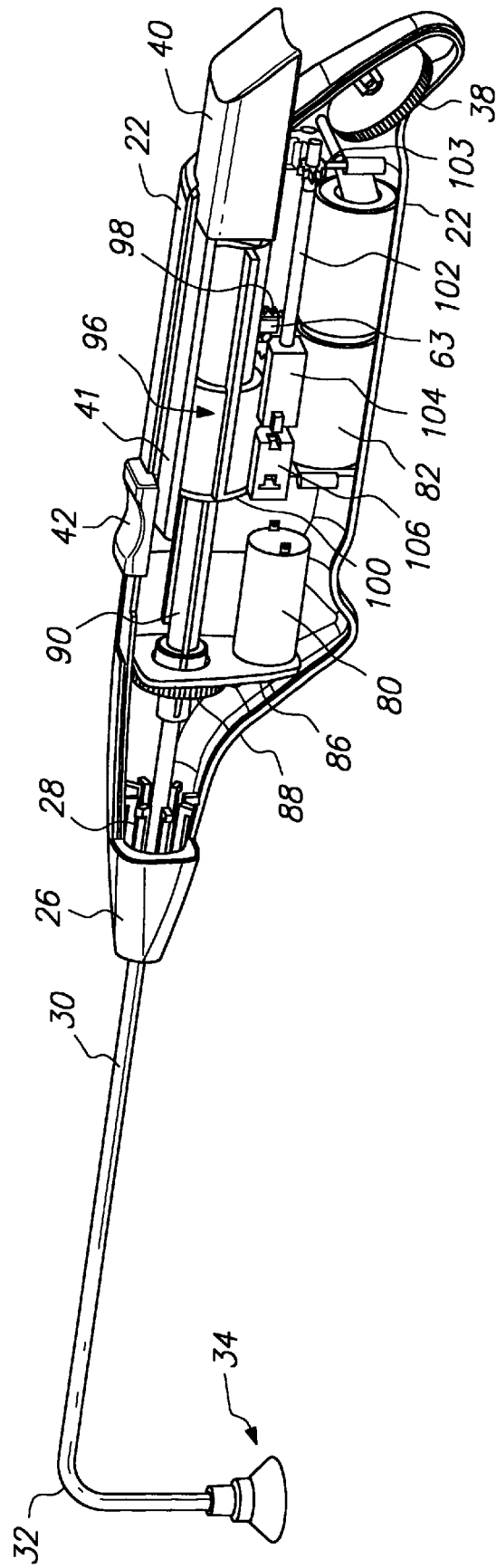
FIGS. 2A and 2B are, respectively, side views taken from generally rear and front perspectives with the side of the housing removed.
Figure 2B:
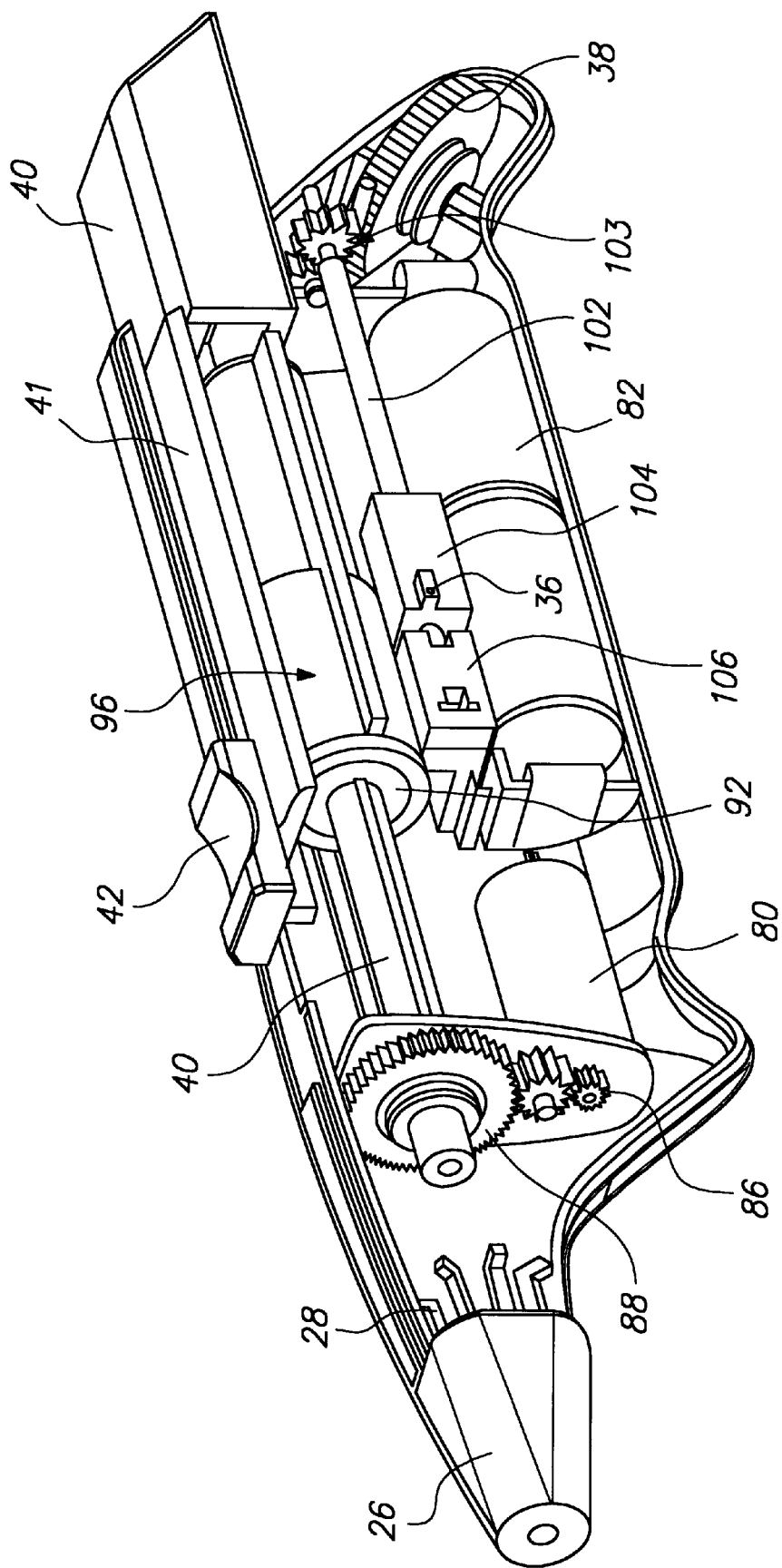
Figure 2C:
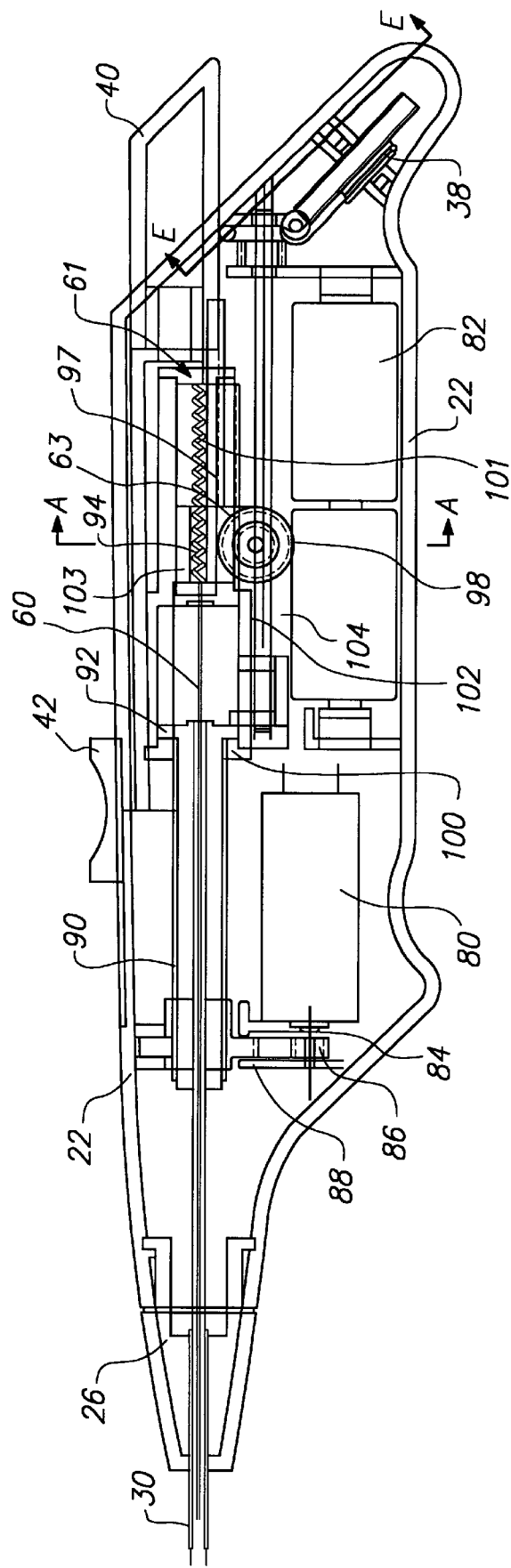
Figure 2E:
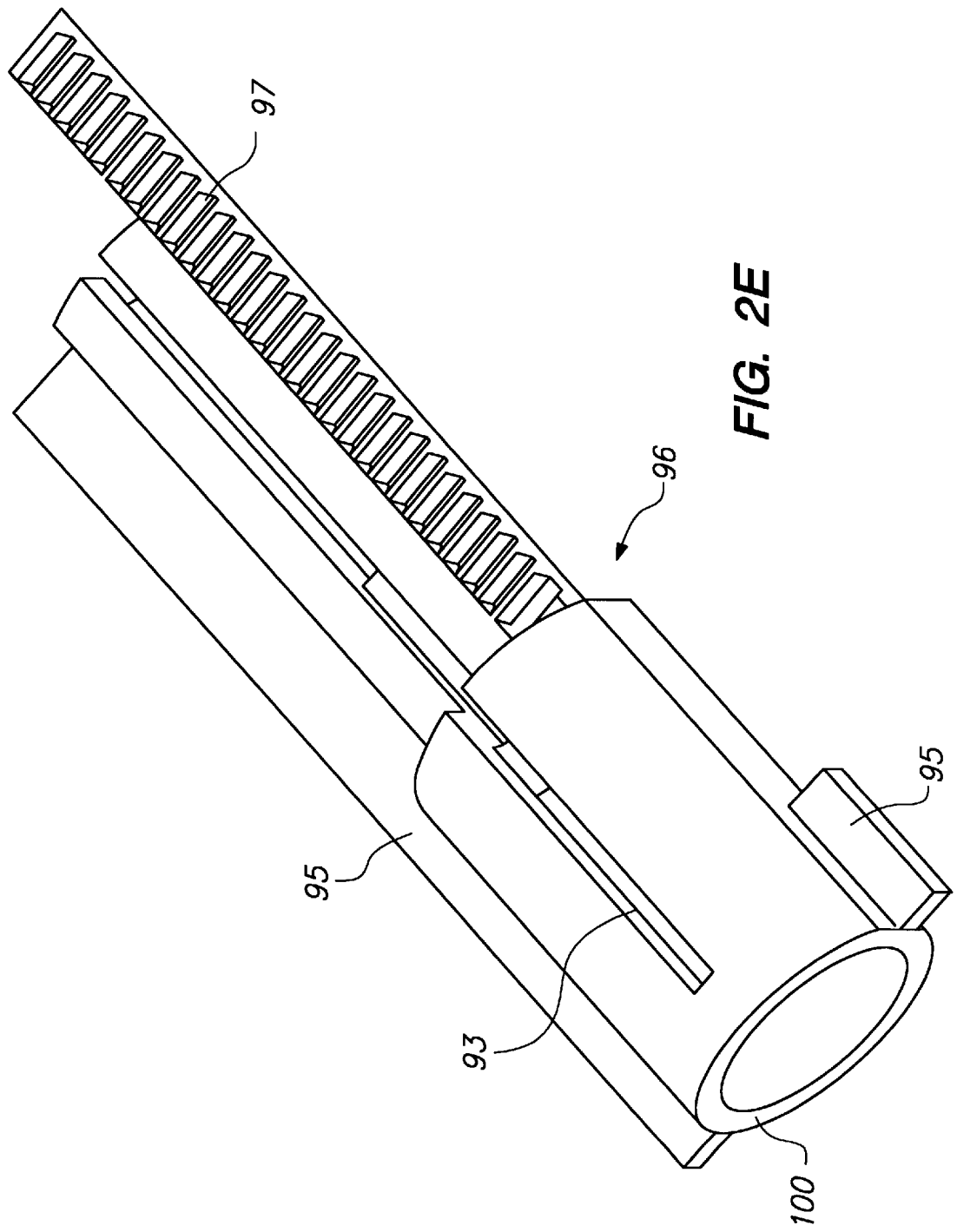
FIG. 2E is a perspective view of the sequencing bar showing the gear rack and slot.
Figure 3:
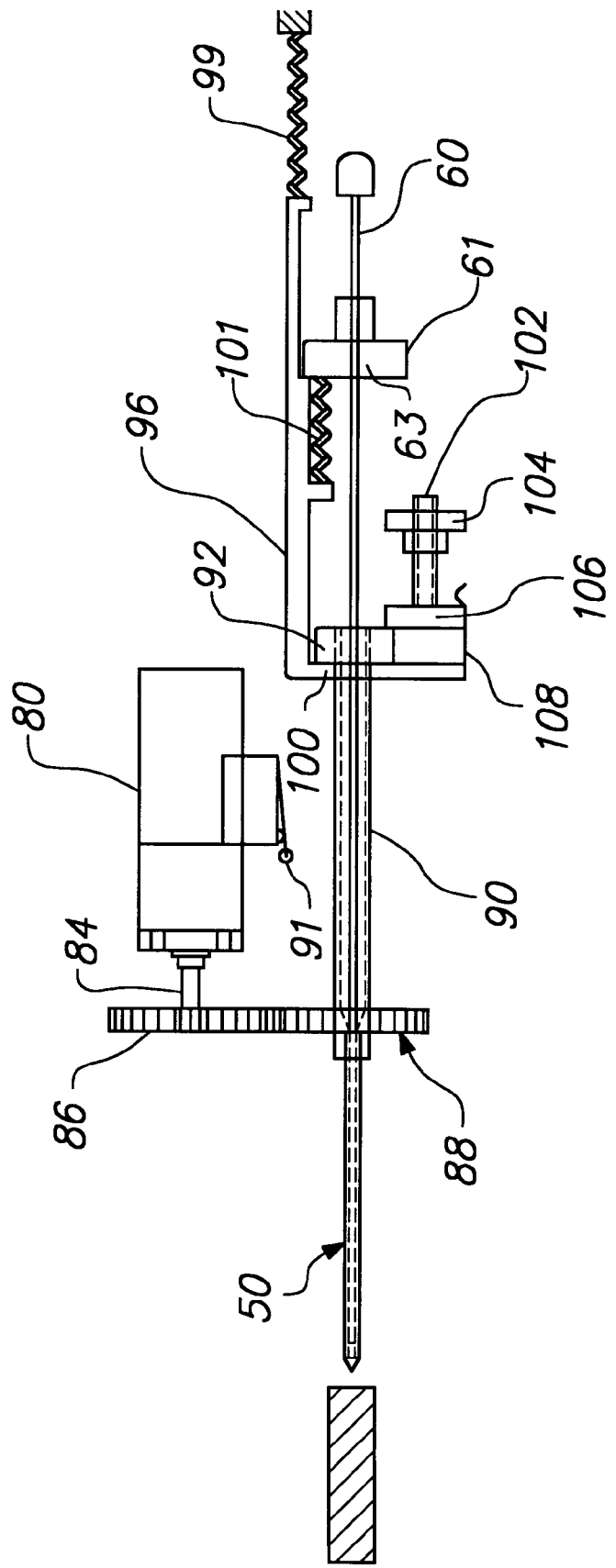
FIG. 3 is a mechanical schematic view of the major components and component relationships of the mechanical cardiac tissue removal device.

FIGS. 2A–2E show the major components for controlling the cutting-tip assembly 50 of the cardiac tissue removal device 20, and FIG. 3 shows such components diagrammatically to illustrate the operating relationships between the components. The semi-automatic operation of the cardiac tissue removal device sequentially activates the components to accomplish a pathway forming sequence.

Beginning with activation by the user of either button 40 or 42, linear movement of the non-actuated button occurs because the two buttons 40, 42 are connected by a shaft 41. The shaft 41 is a generally L shaped bar which is connected to the primary operating component of the device 20, a sequencing bar 96, by a gear mechanism 44 mounted on the shaft 41 as best shown in FIG. 2E. The gear mechanism 44 engages the smaller one of a cluster gear 98 operatively attached to a gear rack of the sequencing bar 96. The cluster gear mechanism 98 allows a relatively short button stroke to produce a longer travel distance of the sequencing bar 96 which is attached to the larger gear of the cluster gear 98.

The sequencing bar 96 is best shown in FIG. 2E and is the primary movable component which sequentially controls movement and operation of other components, including the cutting tip assembly 50. The sequencing bar 96 is a generally tubular structure defining flanges and slots designed to sequentially and separately control movement of the stylet 60 and the hypotube 70 relative to the sequencing bar 96 as the bar 96 is advanced. Axially extending flanges 95 secure positional alignment of the sequencing bar to the housing 22 by being slidably engaged in housing slots 23, as best shown in FIG. 2D. Referring now also to FIG. 2C showing some of the interior components of the sequencing bar, a ferrule 94 within a pocket 103 is used to attach one end of a spring 101 to the sequencing bar 96. The opposite end of the spring 101 is connected to a cap 61. When the sequencing bar 96 moves axially towards the distal tip of the device 20, the stylet 60 is pushed along with the bar by the spring 97, as best shown in FIG. 2C. A slot 93 in the sequencing bar 96 is provided for travel of a stylet stop 63 associated with the ferrule 94, pocket 103 assembly. The stop 63 prevents further advancement of the stylet 60 relative to the sequencing bar 96 when the stop 63 contacts a portion of the depth control mechanism as described below. Also described below, axle 90 is then pushed forward when sequencing bar 96 comes into contact with flange 92. Tab 63 contacts flange 61 in slot 93 to stop movement of axle 90.

The sequencing bar 96 further defines an axle stop 100 which limits axial travel of an axle 90. A return spring 99 also may be provided on the sequencing bar 96 and attached to the housing of the device, or to the button 40, to bias the sequencing bar 96 in its most proximal position when force is released from button 40 or 42.

Figure 1D:
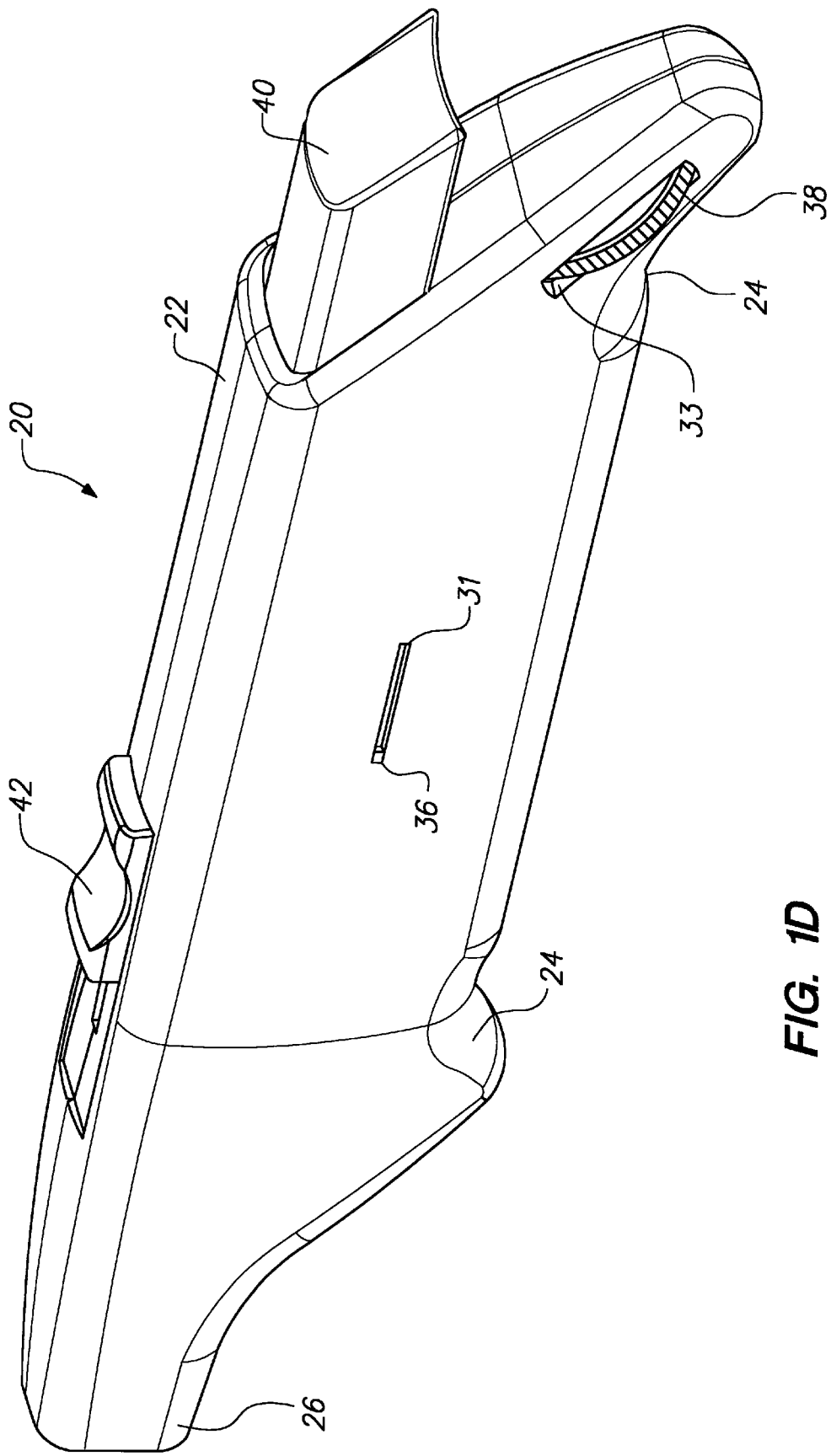
FIG. 1D is a rear side, perspective view of just the proximal portion of the handpiece of the device showing the depth control actuator and gauge.

Maximum travel distances into tissue by the hypotube 70 and the stylet 60 are controlled by the travel of the sequencing bar 96 as controlled by the operator using depth setting mechanism, FIGS. 1D and 2F, as described above, which extends through the housing to a depth adjustment assembly comprising, for example, an adjustment screw 102 and nut 104, as shown in FIGS. 2A–2D, and FIG. 3. Movement of the thumb wheel 38 which is attached to a pulley or gear mechanism 103 with an O-ring, causes the gear mechanism, which is attached to the threaded portion of screw 102, to rotate the adjustment screw 102 to change the position of the nut 104 which serves as a stop for the stylet 60 as best shown in FIG. 2D. The position of the nut 104 is adjusted relative to a stop axle mechanism 106. Releasably connected to the stop axle mechanism is a spring detent 108 (FIG. 3). The depth adjustment assembly affects travel distance of both the stylet 60, as the stylet contacts nut 104, and ultimately the hypotube 70 attached thereto using one setting, depth setting mechanism 36, 38. The detent 108 pulls the depth adjustment assembly along with the moving sequencing bar until contact occurs with a stationary rib on the housing 22. Alternative depth stop mechanisms may be used, including but not limited to a ratchet or cammed mechanism, and discrete stops may be provided.

The semi-automatic operation is provided by a small motor 80, for example a Micro-Mo 6 Volt DC motor, powered by a battery 82, such as a Duracell™ 2/3A Li/MnO2 battery, or may have an air, fluid, or other known actuation mechanism to cause rotation. Operation of the motor 80 causes rotation of an armature shaft 84 which terminates in a drive gear mechanism having 1 or more gears such as spur gears 86, 88. Gear 88 attaches, and is preferably keyed, to an axle 90. Rotation of the gears 86, 88 transmits torque and rotational movement in a clockwise or counter-clockwise direction to the hollow axle 90 which defines a proximal flange 92 and houses the cutting tip assembly 50. Activation of the motor 80 occurs only when electrical contact is made between the sequencing bar 96 and a contact plate of the motor 80 to complete a circuit between the motor 80 and batteries 82. Alternatively, a contact switch 91 may be used and is tripped as shown in FIG. 3 when contacted by a sequencing bar 96.

Figure 4A:
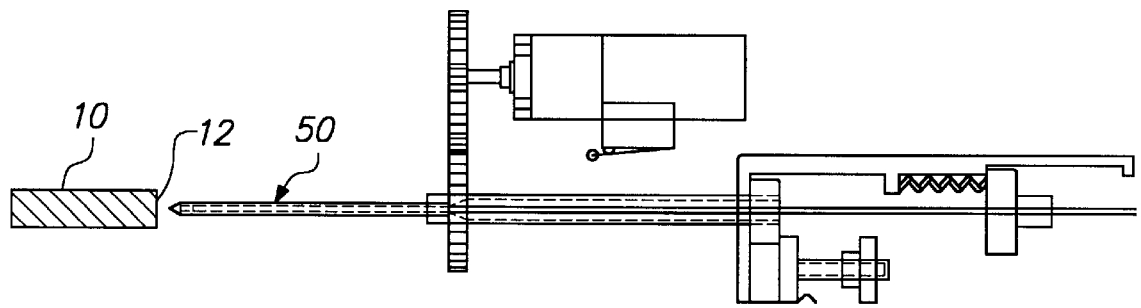
FIGS. 4A–4G are mechanical schematic views similar to FIG. 3 and illustrating changing component relationships during the various stages of formation of a myocardial revascularization pathway.
Figure 4B:
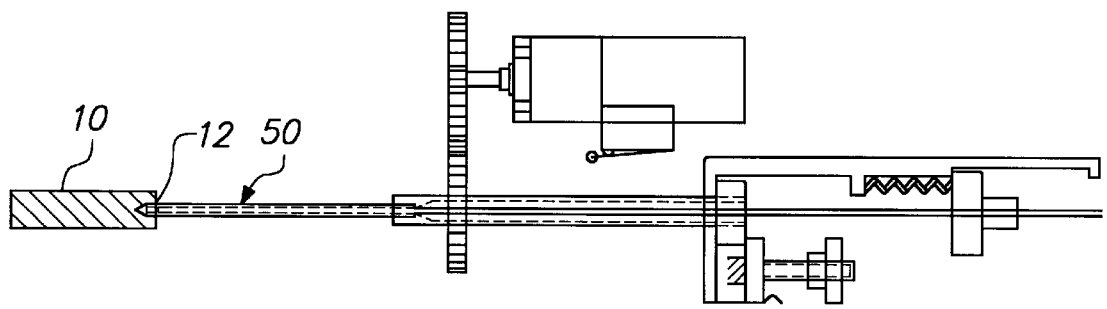

Operation of the cardiac tissue removal device 20 to form a pathway and/or obtain a biopsy sample is best illustrated in FIGS. 4A–4G and FIGS. 7A–7F. In FIGS. 4A and 7A, the cutting tip assembly 50 is shown positioned over a wall of the heart, in this case, the epicardium 12, prior to initiating pathway formation. The hypotube is positioned over and around the plug 64. FIGS. 4B and 7B show initiation of pathway formation by pushing button 40 or 42 to insert the cutting tip assembly 50 through the epicardium 12 so that the piercer can spread the epicardium apart and allow entry of the distal end of the hypotube 70 through the epicardium with minimal trauma thereto. Following placement of the cutting tip assembly 50 within myocardium, continued pressing of button 40, 42 activates only the sequencing bar 96 to set into motion an entire sequence of events resulting in formation of a pathway.

Figure 4C:
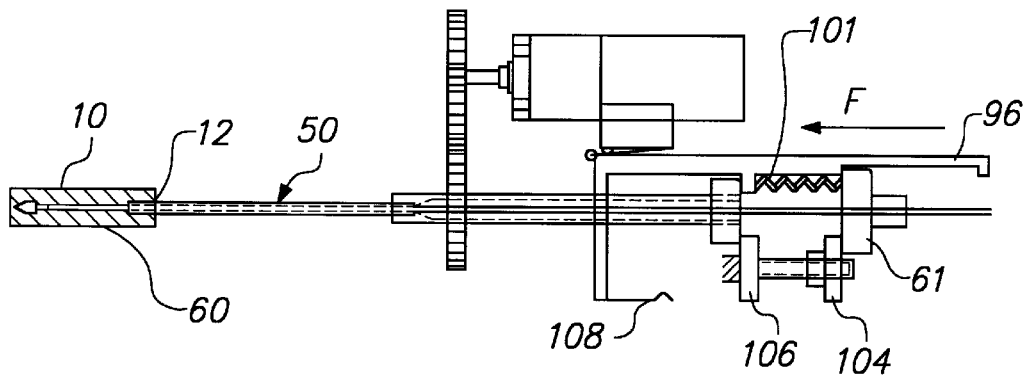
Figure 4D:
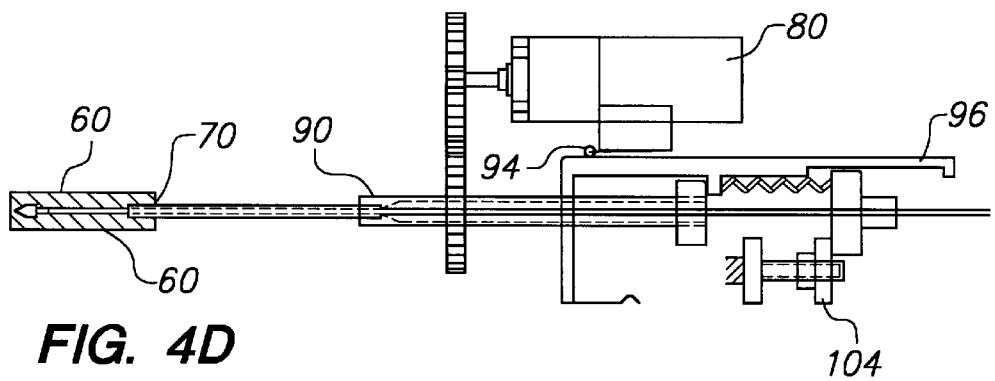
Figure 4E:
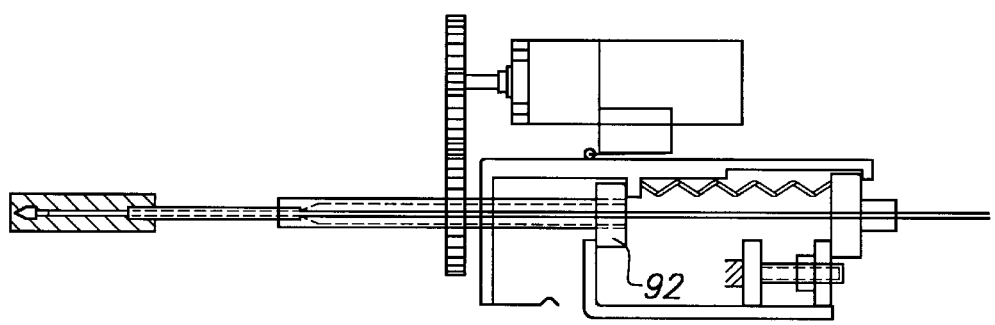

FIGS. 4C and 7C show advancement of the stylet 60 to its maximum depth by depressing push button 40. As the sequencing bar 96 advances in direction "F", the detent 108 is pulled forward and disengages from the axle stop 106 and the stylet 60 is pushed in direction "F" by spring 101. The stylet 60 advances and spreads the myocardium 10 until it reaches the preset distance, determined by the depth setting mechanism, and the stop 63 engages nut 104. As shown in FIGS. 4D and 7D, when the push button 40 is fully actuated, the still advancing sequencing bar 96 makes electrical contact with the motor 80 to cause rotation of the axle 90 and hypotube 70 as the needle 70 begins to advance behind the stylet 60. As the hypotube 70 rotates and advances, the excised tissue is held stationary by the stylet 60 until the hypotube 70 reaches its maximum depth, as shown in FIGS. 4E and 7E, when the axle flange 92 contacts the stop mechanism.

At maximum depth, rotating edge 78 of the hypotube and the contiguous wall of stationary body 66 of the stylet together produce a clean finishing cut to complete a pathway. The excised tissue, including any trimmed tissue captured between the hypotube and the stylet body 66, is held by the stylet rod 62 within the reservoir. Upon removal of the cardiac tissue removal device from the pathway, as shown in FIG. 7F, the excised tissue 120 is completely removed producing a pathway 18 formed completely within the myocardium 10. The pierced, spread opening through the epicardium 12 closes.

Figure 4F:
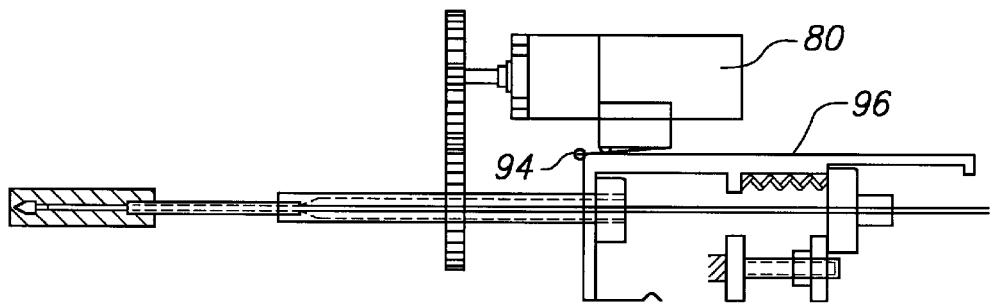
Figure 4G:
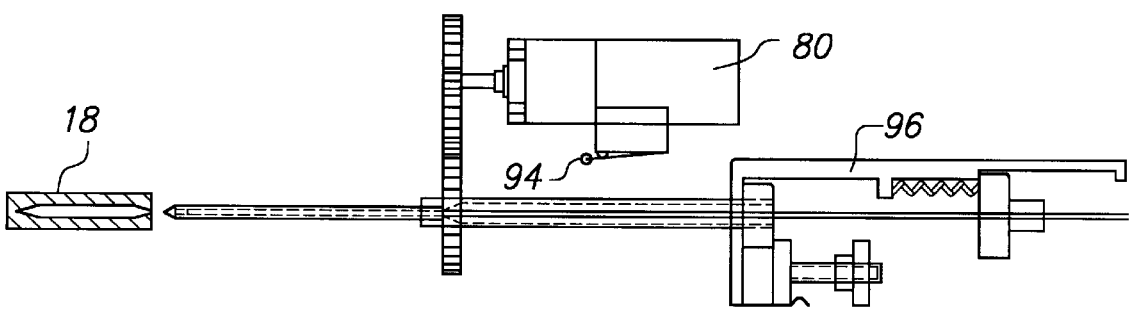

Release of the push button 40 causes the biasing return spring 99 to retract the sequencing bar 96 and, during the first half of the retraction cycle, maintains the relative positions of the stylet and hypotube thereby maintaining the integrity of the tissue reservoir. As shown in FIGS. 4F and 4G, the motor 80 shuts off when the sequencing bar 96 clears the micro switch 94 and the components return to the initial starting positions at the end of the retraction cycle. Alternatively, the cutting tip assembly 50 may be retracted by reversing the direction of travel of the buttons 40, 42.

The reservoir of the cardiac tissue removal device is suitable for storage of multiple tissue samples prior to cleaning, which is particularly suitable when the formed pathways do not communicate with the ventricle, or the tissue may be manually removed from the stylet between formation of pathways to reduce any risks of emboli when the formed pathways communicate with the ventricle. The stylet 60 may be removed from the cardiac tissue removal device for cleaning, or the user may wipe the stylet rod to remove excised tissue. The procedure described above is an example only. Suction may be applied if desired during pathway formation and drugs such as VEGF may be deposited in the pathways to stimulate angiogenesis.

Several alternative hand piece designs for the cardiac tissue removal device are shown in FIGS. 8A through 8E, although other configurations may be used.

The creation of viable pathways using the cutting tip assemblies, with or without the hand pieces discussed above, may by performed by first heating one or more of the cutting tip assembly to a temperature of at least 60 degrees Celsius. This provides thermal damage to the heart wall 10, in addition to the thermal damage created from frictional engagement of the cutting tip assembly. The use of heat simulates the thermal shock of the prior art laser methods. A separate heating element(not shown), such as a conventional thermal band(not shown) may be provided to ensure that each cutting tip assembly is heated. Alternatively, a plurality of detachable stylets may be heated in an oven or heating block(not shown) and attached with a snap lock or quick disconnect mechanism to the hand piece.

Referring once again to FIG. 5, it will be recognized by those skilled in the art that the torquable shaft portion may be extended the length of the cutting tip assembly to create a flexible assembly for insertion through a catheter to form pathways from the inside of the left ventricle of the heart. In such an embodiment, a steerable or torquable catheter is inserted conventionally through the vasculature, perhaps through the femoral artery, into the ventricle using a conventional guidewire. Following positioning within the ventricle, the guidewire is removed and the torquable cutting tip assembly is introduced to the ventricle for creation of pathways. Control of the device is accomplished using an exterior handpiece having the components described herein, particularly the depth control mechanism to ensure the created pathways do not penetrate the epicardium.

As will be understood by those familiar with the art, the present invention may be embodied in other specific forms without departing from the spirit or essential characteristics thereof. For instance, both the stylet and the hypotube may rotate during at least part of a sequence and the sequencing bar may be altered to trigger rotation and advancement of the hypotube close behind the advancing stylet. Other configurations of the distal end of the stylet and the cutting edge of the hypotube may be used to create cooperating geometries. The motor may be configured to require operator activation instead of being automatically tripped, and suction may be used for removal of excised tissue from the stylet. The housing may be made of materials other than plastic and may be configured differently to provide alternative designs. The scope of the present invention is therefore limited only by the scope of the claims appended hereto.

What is claimed is:

1. A tissue removal device comprising:
   a housing;
   a cutting assembly extending from the housing, the cutting assembly having a tissue storage mechanism for holding tissue both during and following mechanical cutting thereof by the cutting assembly;
   a tissue piercing and stabilization member slidingly mounted within the cutting assembly; and
   an advancement mechanism within the housing for advancing the cutting assembly over the tissue piercing and stabilization member.

2. The device of claim 1 wherein the cutting assembly comprises a hollow tube having an internal bore and the tissue piercing and stabilization member is a stylet mounted within the internal bore.

3. The device of claim 2 wherein the advancement mechanism is attached to the cutting assembly and the tissue piercing and stabilization member and comprises a rotation mechanism and a translation mechanism.

4. The device of claim 3 further comprising a power source within the housing for operating at least the rotation mechanism.

5. The device of claim 4 further comprising an output shaft attached to the power source; gear mechanisms attached to the output shaft, the gear mechanisms causing rotation of the hollow tube axially into the tissue; a sequencer traveling within the housing for activating the power source and for moving the tissue piercing and stabilization member and the cutting assembly axially into the tissue; and stops for selectively setting a maximum depth of advancement of the cutting assembly into the tissue.

6. The device of claim 5 wherein the advancement mechanism is a semi-automatic interlock mechanism which provides successive movement of the tissue piercing and stabilization member and the cutting assembly.

7. The device of claim 6 further comprising an actuator on the housing, wherein actuation of the actuator causes axial movement of the sequencer which causes successive linear movement of the tissue piercing and stabilization member and the cutting assembly and actuation of the power source.

8. The device of claim 7 wherein the stops control an amount of axial movement of the sequencer and the tissue piercing and stabilization member and the cutting assembly.

9. The device of claim 3 wherein the housing defines a finger grip surface, the housing further having a depth stop setting mechanism and at least one actuation button.

10. The device of claim 3 wherein the rotation mechanism rotates the hollow tube and the stylet.

11. The device of claim 2 wherein the stylet defines a distal body having (1) a piercing tip , (2) a proximal tapered surface for alignment of the cutting assembly, and (3) a central diameter selected to fit closely within the bore thereby cooperating with the hollow tube to cut tissue and form a tissue chamber.

12. The device of claim 2 wherein the hollow tube further defines a beveled cutting edge and the stylet defines a distal end defining a cooperating cutting surface contiguous to the beveled cutting edge of the hollow tube.

13. The device of claim 12 wherein the cutting assembly defines a generally closed chamber when the hollow tube is advanced over and around the stylet distal end.

14. The device of claim 12 wherein the hollow tube and the stylet further comprise flexible portions and are sized to slidingly fit within a guide catheter for introduction through the vasculature into a heart chamber.

15. The device of claim 2 further comprising at least one drug delivery and suction conduit within the housing and operatively connected to the hollow tube.

16. The device of claim 1 further comprising a heating device connected to the cutting assembly.

17. The device of claim 1 wherein the housing further comprises a rotatable nose piece and a hollow shaft extending from the nose piece, the shaft defining a bend, the cutting assembly mounted within the shaft.

18. The device of claim 1 wherein the housing further comprises a hollow shaft extending axially from the housing to an articulating joint for changing an angle of orientation of the cutting assembly mounted within the hollow shaft.

19. The device of claim 1 wherein the housing further defines a shaft extending therefrom and a distal tip attached to a distal end of the shaft, the distal tip comprises a tissue contacting surface.

20. The device of claim 19 comprising one or more interchangable, detachable distal tip.

21. The device of claim 19 wherein the distal tip is sized to fit through a conventional port used in a minimally invasive surgical procedure.

22. The device of claim 1 wherein the advancement mechanism further comprises a depth stop assembly for controlling advancement depth of the cutting assembly, the depth stop assembly having a depth selection setting.

23. A mechanical tool for removing cardiac tissue and forming revascularization pathways in a heart comprising:
   a distal piercing tip for piercing cardiac tissue along an axis;
   a cutting assembly advancable along the axis of the distal piercing tip;
   a storage mechanism for holding cardiac tissue both during and following mechanical cutting by the cutting assembly; and
   an advancement mechanism for advancing the cutting assembly through the cardiac tissue towards the distal piercing tip, the cutting assembly allowing removal of cardiac tissue to form a revascularization pathway, and the storage mechanism allowing collection of the removed cardiac tissue.

24. The tool of claim 23 further comprising a housing having a flexible tube extending therefrom and a flexible guiding catheter sized for extension through the vasculature into a chamber of the heart, the guiding catheter defining a lumen for extension therethrough of the flexible tube from the housing, the flexible tube bearing the cutting assembly.

25. The tool of claim 23 further comprising a housing having a shaft with an articulating joint and a cardiac wall contact surface for stabilizing the tool on a beating heart, the cardiac wall contact surface defining an aperture therethrough, the cardiac wall contact surface is connected to the articulating joint, and the joint, contact surface and shaft are sized to fit through a conventional port used in a minimally invasive surgical procedure.

26. A method for obtaining a cardiac tissue sample and creating pathways in the wall of the cardiac muscle appropriate for transmyocardial revascularization, the method utilizing an actuator and a cutting assembly having a stylet mounted within a rotating hypotube, the method comprising:

positioning the cutting assembly on a wall of the heart;
moving the actuator to translate the stylet a preset distance into myocardium;
moving the actuator further to initiate movement of the hypotube into an opening created by the stylet;
moving the actuator further to activate a power source to cause the hypotube to rotate to excise cardiac tissue;
moving the actuator to a preset point to cause the actuator and stylet to cleanly finish cutting the cardiac tissue; and
removing the cutting assembly from the heart, with excised cardiac tissue trapped within a chamber formed by the hypotube and stylet and leaving a revascularization pathway.

27. The method of claim 26 further comprising the step of heating at least the hypotube to a temperature of at least 60 degrees Celsius.

28. The method of claim 26 further comprising the step of inserting a drug into the created pathway through the hypotube.

29. The method of claim 26 further comprising a guide catheter, the method further including the following steps:
   inserting the guide catheter percutaneously through the vasculature into a left ventricle of the heart;
   inserting the cutting assembly through the guide catheter into the left ventricle for removal of heart tissue and formation of pathways from the inside of the heart.

30. The method of claim 26 further comprising the steps of:
   inserting one or more conventional minimally invasive surgical ports between ribs of a patient; and
   inserting the cutting assembly through one of the ports until a distal tip thereof contacts the heart.

31. The method of claim 26 further comprising the steps of applying suction to maintain the cutting assembly on the wall of the heart and to assist in excising the cardiac tissue.

32. A method of operating a cardiac tissue removal device having a housing, a push button, a power source, a sequencer, gears, a depth stop mechanism, and an extendable cutting assembly comprising the steps of:
   setting a desired depth of tissue penetration using the depth stop mechanism;
   pushing the push button to translate the sequencer axially;
   continuing to push the button to cause the sequencer to move further axially until the sequencer causes a stylet of the cutting assembly to move axially into tissue;
   further pushing the button to cause the sequencer to begin moving a needle surrounding the stylet into the tissue behind the stylet, the sequencer further activating the power source which causes a needle to rotate while advancing; and
   advancing the button until the sequencer contacts one or more stops to control distances of advancement of the stylet and rotating needle.

* * * * *